United States Patent
Schick et al.

[11] Patent Number: 5,852,647
[45] Date of Patent: Dec. 22, 1998

[54] METHOD AND APPARATUS FOR MEASURING BONE DENSITY

[75] Inventors: David B. Schick, Flushing; David B. Plass, Merrick; Jonathan Singer, Dobbs Ferry, all of N.Y.

[73] Assignee: Schick Technologies, Long Island City, N.Y.

[21] Appl. No.: 936,571

[22] Filed: Sep. 24, 1997

[51] Int. Cl.$^6$ .................................................. G01N 23/06
[52] U.S. Cl. ............................ 378/53; 378/56; 378/207
[58] Field of Search .................... 378/53, 51, 54, 378/56, 98.8, 207, 162

[56] References Cited

U.S. PATENT DOCUMENTS

| | | | |
|---|---|---|---|
| 3,944,830 | 3/1976 | Dissing | 250/358 R |
| 3,996,471 | 12/1976 | Fletcher et al. | 250/444 |
| 4,811,373 | 3/1989 | Stein | 378/54 |
| 4,903,203 | 2/1990 | Yamashita et al. | 364/413.15 |
| 4,947,414 | 8/1990 | Stein | 378/55 |
| 4,986,273 | 1/1991 | O'Neill et al. | 128/653 R |
| 5,040,199 | 8/1991 | Stein | 378/56 |
| 5,122,664 | 6/1992 | Ito et al. | 250/327.2 |
| 5,187,731 | 2/1993 | Shimura | 378/207 |
| 5,253,282 | 10/1993 | Pelc | 378/99 |
| 5,270,651 | 12/1993 | Wehrli | 324/308 |
| 5,335,260 | 8/1994 | Arnold | 378/207 |
| 5,365,564 | 11/1994 | Yashida et al. | 378/56 X |
| 5,400,377 | 3/1995 | Hu et al. | 378/8 |
| 5,402,781 | 4/1995 | Dimarogonas | 128/653.1 |
| 5,465,284 | 11/1995 | Karellas | 378/62 |
| 5,473,655 | 12/1995 | Hu | 378/4 |
| 5,480,439 | 1/1996 | Bisek | 623/16 |
| 5,533,084 | 7/1996 | Mazess | 378/54 |
| 5,577,089 | 11/1996 | Mazess | 378/54 |
| 5,696,805 | 12/1997 | Gaborski et al. | 378/56 X |
| 5,712,892 | 1/1998 | Weil et al. | 378/56 X |

OTHER PUBLICATIONS

M.L. Bouxsein, et al., "Precision and Accuracy of Computed Digital Absorptiometry for Assessment of Bone Density of the Hand", vol. 7, No. 5, 1997, pp. 444–449, Osteoporosis International. No Month.

*Primary Examiner*—David P. Porta
*Attorney, Agent, or Firm*—Fitzpatrick, Cella, Harper & Scinto

[57] ABSTRACT

A method and apparatus for measuring bone density is disclosed. The method and apparatus use high-energy and low-energy images of hard-tissue and soft-tissue references to determine characteristics of hard and soft tissue under high-energy and low-energy radiation. Then, high-energy and low-energy x-ray images of the subject are processed to compute the density of the bone inside the subject.

55 Claims, 4 Drawing Sheets

METHOD AND APPARATUS FOR MEASURING BONE DENSITY

BACKGROUND OF THE INVENTION

1. Field of the Invention

This invention relates to a method and apparatus for measuring the density of bones. More specifically, it relates to a method and apparatus for measuring the density of bones that are inside a body, using dual-energy x-ray absorptometry (DEXA), and processing the dual-energy images to determine the bone density.

2. Description of the Related Art

Osteoporosis is a disease in which the calcium content of a person's bones is gradually reduced. This leads to an increased risk of fractures, particularly in the spine, hip and wrist. Osteoporosis is particularly common in post-menopausal women. It has been estimated that approximately 40,000 American women die per year from complications due to osteoporosis.

an Ordinary x-rays images cannot be used to provide an accurate measurement of bone density because the bones (hard tissue) are surrounded by skin, muscle, tendons, etc. (soft tissue) that also contribute to the x-ray image.

One existing technique for detecting the mineral loss from a person's bones is dual-energy x-ray absorptometry (DEXA). DEXA uses two x-ray images obtained using x-rays with different energy levels to compensate for tissue variations and quantify bone mass in an x-ray image. Typical existing DEXA systems rely on known x-ray absorption characteristics of hard tissue and soft tissue to both high-energy and low-energy radiation. This enables existing DEXA systems to set up the following pair of equations which can then be solved to determine the hard tissue mass:

$$IH = (m_H * \mu H_H) * (m_S * \mu H_S)$$

and $$IL = (m_H * \mu L_H) * (m_S * \mu L_S)$$

where IH is the measured high-energy image pixel; mH is the mass of the hard tissue of the pixel; $m_S$ is the mass of the soft tissue of the pixel; $\mu H_H$ and $\mu H_S$ are the high-energy mass absorption coefficients for the hard tissue and soft tissue, respectively; and $\mu L_H$ and $\mu L_S$ are the low-energy mass absorption coefficients for the hard tissue and soft tissue, respectively. Because all of the $\mu$ coefficients are known in advance, there are only two unknowns in this set of two equations, which can be easily solved using conventional techniques.

This arrangement, however, has a significant drawback because it uses a set of constants for the $\mu$ coefficients. Using constants for the $\mu$ coefficients would provide an accurate result if the high-energy and low-energy radiation each consisted of a very narrow band of frequencies centered about an ideal center frequency. But with almost all practical radiation sources, neither of these factors is guaranteed: the center frequency of the radiation can vary significantly, and the bandwidth of the radiation is usually wide. These real world factors reduce the accuracy of traditional DEXA systems that use these two equations as a model.

Some existing DEXA systems use an x-ray image of a wedge of material with bone-like x-ray attenuation properties (e.g., aluminum) to calibrate the system, where the thickness and density of each part of the wedge is known in advance. But this approach does not compensate for all of the potential sources of error.

Existing DEXA measurements also require expensive equipment that is usually available only in specialized facilities. This equipment is typically complex, and the test results must be interpreted by a skilled person (e.g., a radiographer), resulting in a number of additional drawbacks: First, the cost of labor associated with the radiographers is significant. In addition, because the test results must be interpreted by humans, existing tests are not highly repeatable. More specifically, because judgment is involved, two radiographers may reach different conclusions as to the actual bone density when interpreting identical data. This is particularly problematic when measuring the bone density of a single patient over a period of time, such as one year intervals, to determine the progression of bone loss. It would be advantageous to remove these human variations, to determine more accurately the progression of osteoporosis over time.

The need for the interpretation of test results also makes it more difficult to return these results to the patient instantly. It would be advantageous to measure bone density as easily as taking a blood pressure reading. No previous systems exist, however, that can provide a readout of bone density, with minimal human intervention, by simply inserting a patient's hand into a fixture and pressing a few buttons. There is therefore a need for an improved bone density measurement system that departs significantly from existing systems.

SUMMARY OF THE INVENTION

According to one aspect of the invention, a method of measuring the density of a bone in a body part from high-energy and low-energy images of the body part and a pair of references is provided. The method includes the steps of determining high-energy and low-energy radiation transmissivity characteristics of varying thicknesses of the hard tissue reference and the soft tissue reference from the high-energy and low-energy images, and determining the density of the bone based on at least one pixel that corresponds to bone in the high-energy image, a corresponding pixel (or pixels) in the low-energy image, and the determined transmissivity characteristics. A corresponding apparatus is also provided.

According to another aspect of the invention, a method of measuring the density of a bone in a body part is provided. The method includes the steps of obtaining high-energy and low-energy images of the body part together with hard and soft tissue references by irradiating them with high-energy and low-energy radiation, and determining high-energy and low-energy radiation transmissivity characteristics of varying thicknesses of the hard tissue reference and the soft tissue reference from the high-energy and low-energy images. The density of the bone is determined based on at least one pixel that corresponds to bone in the high-energy image, a corresponding pixel (or pixels) in the low-energy image, and the determined transmissivity characteristics. A corresponding apparatus is also provided.

According to another aspect of the invention, a method of measuring the density of a bone in a body part is provided. The method includes the steps of computing a first function that relates a high-energy radiation transmissivity of a hard tissue reference to a low-energy radiation transmissivity of the hard tissue reference, and computing a second function that relates a high-energy radiation transmissivity of a soft tissue reference to a low-energy radiation transmissivity of the soft tissue reference. The method also includes the steps of selecting a high-energy set of pixels and a corresponding low-energy set of pixels, and computing a hard tissue value for the set of pixels based on the high-energy set, the low-energy set, the first function, and the second function. A third function is computed that relates an amount of radiation transmitted to a given pixel to the thickness of the hard tissue reference above the given pixel, and the bone density is computed based on the third function and the hard tissue value for at least one pixel that corresponds to bone. Another aspect of the invention is similar, but adds the steps of irradiating the body part and the references and detecting the transmitted radiation.

According to another aspect of the invention, a method of determining the radiation transmissivity of a bone in a body part is provided. The method includes the steps of reading at least one pixel of interest in a high-energy image of the body part and a corresponding pixel (or pixels) in a low-energy image of the body part, and accessing stored functions that relate high-energy radiation transmissivity to low-energy radiation transmissivity for a hard tissue reference and a soft tissue reference. A hard tissue value is calculated based on the pixels from the high-energy and low-energy images and the stored functions. A corresponding apparatus is also provided.

According to another aspect of the invention, a method of determining the radiation transmissivity of a bone in a body part is provided. This method includes the steps of estimating a first-energy radiation transmissivity of the first tissue, and determining a first-energy radiation transmissivity of the second tissue based on the first-energy radiation transmissivity of the first tissue and a measured first-energy transmissivity of the pixel of interest. Second-energy radiation transmissivity of the first tissue and the second tissue are calculated based on the first-energy radiation transmissivities and two functions. Then, a composite second-energy transmissivity is calculated based on the second-energy radiation transmissivities of the first tissue and the second tissue. The composite second-energy transmissivity is compared to the measured second-energy transmissivity, and tested for closeness. If they are not sufficiently close, the estimate of the first-energy radiation transmissivity of the first issue is adjusted, and the process is repeated.

DETAILED DESCRIPTION OF THE PREFERRED EMBODIMENTS

Figure 1:
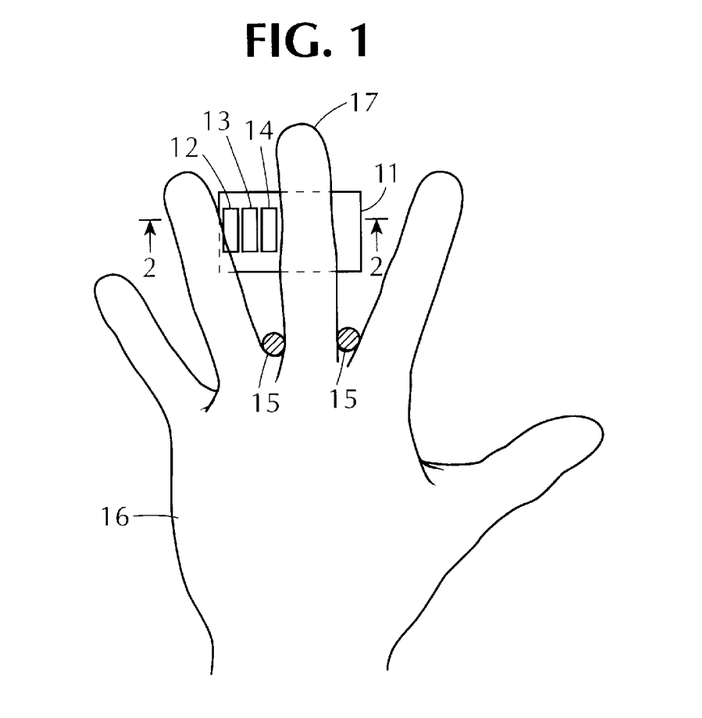
FIG. 1 depicts a bone density measuring device in accordance with the present invention.

FIG. 1 is a top view of the present invention being used to measure the density of a bone in the hand 16 of a patient. A radiation sensor 11 is provided. This radiation sensor, by way of example, may comprise a CMOS active pixel sensor (APS) array or a charge-coupled device (CCD). A layer of a phosphorescent material may be optically coupled to the radiation sensor by a suitable light directing device including, but not limited to, a lens or a bundle of optical fibers, etc. Alternatively, the phosphorescent material may be optically coupled to the radiation sensor directly by depositing the phosphorescent material on the face of the sensor. This phosphorescent material converts incoming x-rays to light, which increases the detection efficiency of the sensor. Examples of suitable phosphorescent coatings include gadolinium oxysulphate, thallium-doped cesium iodide, cadmium telluride, cadmium sulfide, calcium tungstate, zinc sulfide and zinc cadmium sulfide. Scintillating glass (e.g., terbium glass) or scintillating optical fibers may also be used.

Before the x-ray images are obtained, the patient's finger 17 is placed over the sensor 11. A pair of guide pins 15 align the finger 17 to a desired position above the sensor 11. While a preferred position is such that the middle phalange of the middle finger of the patient's non-dominant hand is located directly over the sensor 11 (as explained below), the system can provide a reading when any portion of the patient's bone is placed above the sensor.

A hard tissue reference and a soft tissue reference are also placed over the sensor. The hard tissue reference preferably includes a linear wedge 14 of a material with x-ray absorption characteristics similar to those of human bone, as well as a stepped wedge 12 made of a similar material. The preferred material for these wedges 12 and 14 is aluminum. The soft tissue reference is preferably a linear wedge 13, made of a material with x-ray absorption characteristics similar to those of soft tissue. The preferred material for this wedge is a two-part epoxy made of five parts bisphenol-A epoxy resin and three parts of a low viscosity aminoamine hardener.

Figure 3:
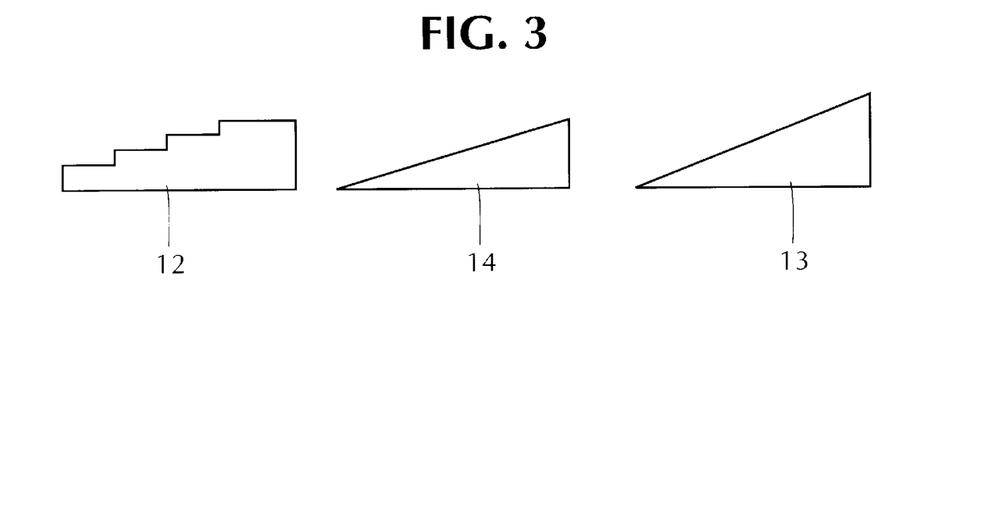
FIG. 3 is a side view of the reference wedges.

FIG. 3 shows the side view of the three wedges 12–14, which illustrates the difference between the linear and the stepped wedges. Each of the steps of the stepped hard wedge 12 has a known thickness. The linear hard wedge 14 and the soft wedge 13 have linear (i.e., not stepped) surfaces.

While the preferred embodiment uses a hard tissue reference that includes two wedges, a single wedge (either linear or stepped) may be used instead. In addition, while the preferred embodiment of the soft tissue reference is a linear wedge, a stepped wedge may be used as well. In an alternative embodiment (not shown), the soft tissue wedge 13 may be omitted, and the actual soft tissue of the patient's finger may be used as the soft tissue reference.

Figure 2:
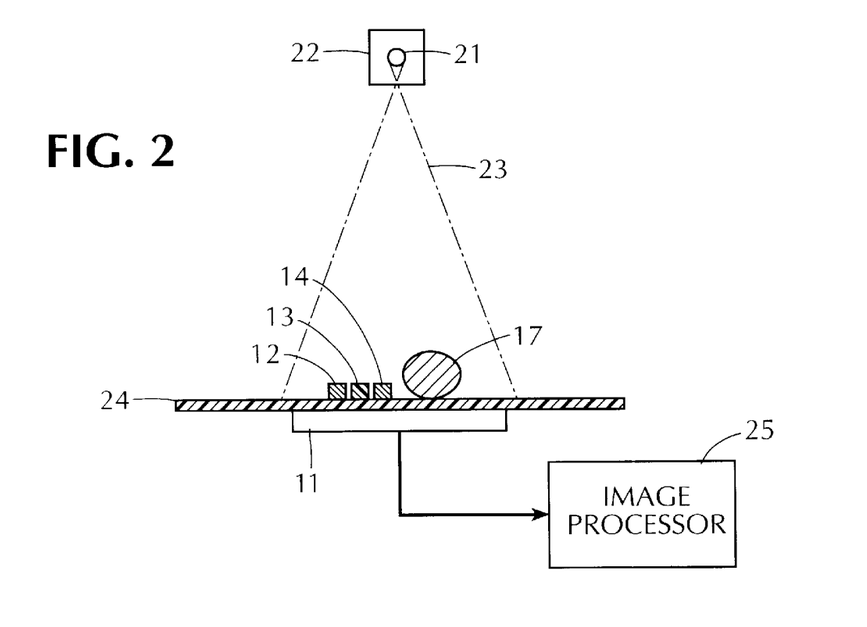
FIG. 2 is a side view of the bone density measuring device, taken along the section line 2—2 shown in FIG. 1.

FIG. 2 shows a side view, taken in section along the section line 2—2 from FIG. 1. Here, the sensor 11, the wedges 12–14 and the finger 17 from FIG. 1 can be seen in section. Also depicted is the x-ray source 21 located above the finger. An optically opaque, x-ray transparent sheet 24 ensures that the image reaching the sensor 11 is an x-ray image of the finger 17 and the wedges 12–14, but is not affected by ambient light. The beam of x-rays emanating from the x-ray source 21 goes through the finger 17 and the wedges 12–14 and strikes the sensor 11. The output from the image sensor 11 is routed to the image processor 25.

During operation of the present invention, the x-ray source is excited to produce, in alternation, x-rays of two different energy levels. First, the x-ray source emits a high-energy radiation that is detected by the sensor 11, producing a high-energy image that is sent to the image processor 25. Next, the x-ray source 21 emits a low-energy radiation that is also detected by the sensor 11, producing a low-energy image that is sent to the image processor 25. These two steps are referably performed in rapid succession to minimize inter-image variations caused by movement of the finger 17 between the high-energy and low-energy exposures.

When emitting high-energy radiation, most x-ray ources also emit a significant amount of low-energy radiation. The contribution of this low-energy radiation can reduce the accuracy of the DEXA process. As a result, it is preferable to insert a high-pass filter into the high-energy beam to reduce these low-energy radiation components and thereby improve the accuracy of the system. A preferred high-pass filter is a piece of Zinc, 0.5 mm thick, that is inserted into the high-energy beam.

If a density measurement of a particular bone is desired, either the high-energy image or the low-energy images may be displayed for operator verification. For example, for the middle phalange of a finger, a displayed image similar to FIG. 6, with the bone lined up vertically, would be acceptable. Alternatively, if the particular bone being imaged is not critical, this display step can be omitted and the image processor can analyze the images without operator intervention. The images are then processed as described below to obtain a numerical measure of the patient's bone density.

Figure 4:
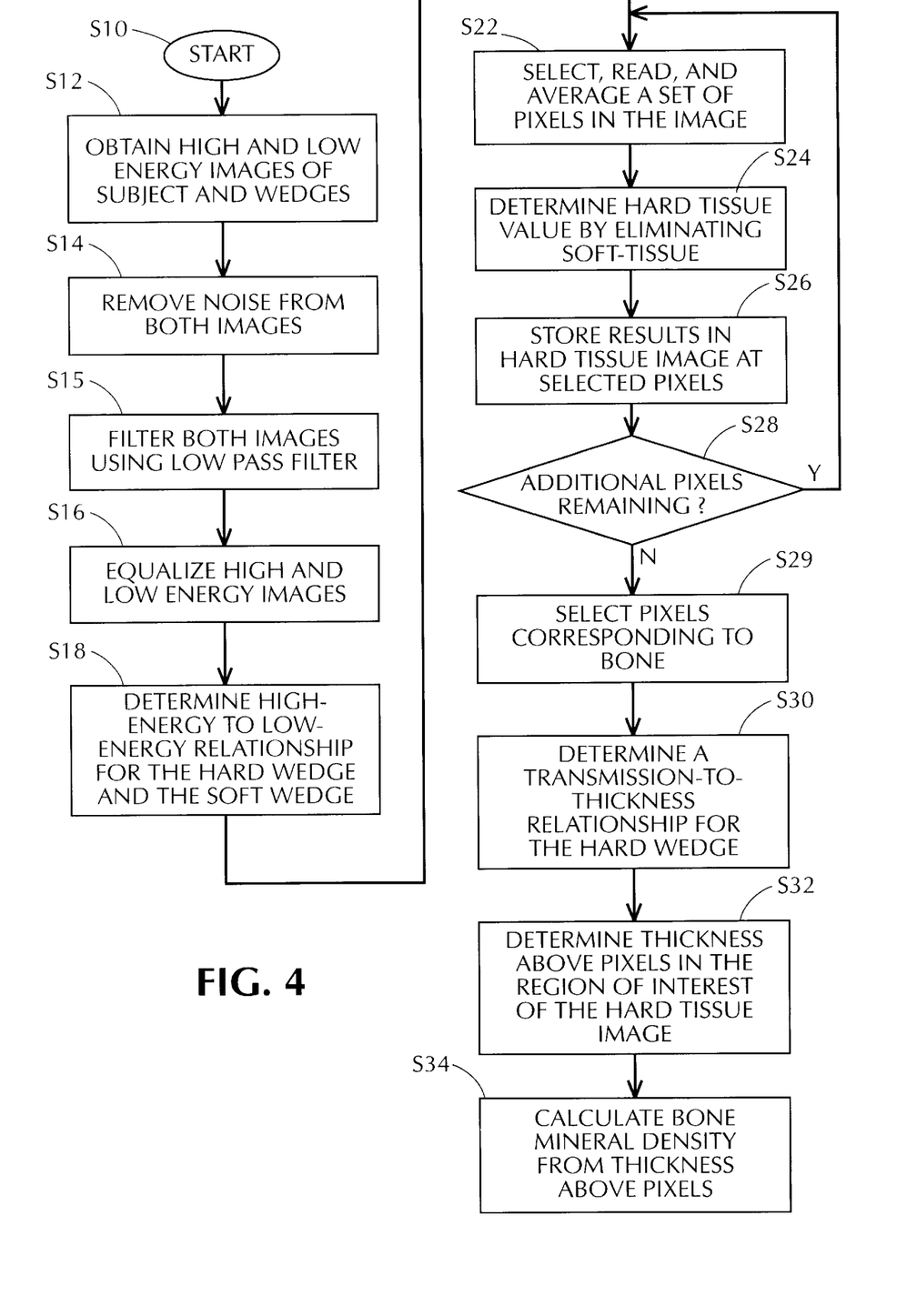
FIG. 4 is a flowchart of a preferred bone density measurement process in accordance with the present invention.

Referring now to FIG. 4, in step S12, the high-energy image and low-energy image are obtained, as described above. In step S14, each of these images is processed by a noise-removal filter to eliminate spots in the image. In step S15, the images are filtered by a low pass filter which preferably averages each pixel with the eight surrounding pixels and assigns the average value to the center pixel. In step S16, the high-energy and low-energy images are equalized based on the air being the darkest pixel value. During this equalization process, the range of data values for the pixels in each image is expanded to make use of the full dynamic range of the data word used to represent the image data. For example, if 12 bit data is used to represent each pixel, and the average value of pixels that correspond to air (and have the highest transmissivity) is 3900, then all the pixels in the image are multiplied by 4095/3900. The post-equalization data values in the images will then range up to 4095, with 4095 representing the average value of pixels that correspond to air. These pixels of air may be taken from predetermined locations of the image. While equalizing based on the pixels of air (those with the highest transmissivity) is preferred, other levels may be used to equalize the image. For example, 4095 may be used to represent 90% transmissivity, and those pixels with greater than 90% transmissivity may be set to 4095. This would, however, destroy some of the information in the image. It will, of course, be recognized that word lengths other than 12 bits may be used by making appropriate adjustments.

In step S18, a first relationship between pixels of the high-energy image and corresponding pixels of the low-energy image is established for the image pixels of the hard tissue reference, and a second relationship is established for the image pixels of the soft tissue reference.

The first relationship for the hard tissue reference is created as follows: For each pixel corresponding to a pixel in the hard tissue reference (which can be found at known locations in the image), the data from the high-energy image is stored in a first array and the data from the low-energy image is stored in a second array. Using well known curve fitting techniques, a relationship is established between the high-energy image data and the low-energy image data. Preferably, a least-squares curve fit of the arrays is used such that $$y = a * x^b$$

where the high-energy image data is used as the 'x' values, the low-energy image data is used as the 'y' values, and a and b are the coefficients selected by the curve fitting process.

When the hard tissue reference includes both a stepped wedge 12 and a linear wedge 14 (shown in FIG. 3), it is preferable to fit the curve to the image data corresponding to the linear wedge.

A look-up table is then produced from the calculated curve for pixel values 0 to 4095 (assuming that 12 bit data is used). If any entry would be less than 0, that pixel is set to 0. If any entry would be greater than 4095, that pixel is set to 4095. It is advantageous to used double precision floating point numbers for this step, rounding the floating point results to the nearest integer value before it is stored in the look-up table. The 'x' values (high-energy values) are then used as the index into the array, which produces a corresponding 'y' value (low-energy value) for any given high-energy value.

A second relationship is then computed for the soft tissue reference using a similar process, and a second look-up table is also created.

When choosing pixels for the high-to-low function or look-up tables, pixels which have less than 25% of the maximum possible intensity value are ignored. This is done because in the low-energy image, the thickest parts of the hard wedge usually have no x-ray penetration and are thus too 'white' (i.e., the pixel data value is too low).

Once the high-energy to low-energy relationships are stored in look-up tables, subsequent access to these relationships can be accomplished by simply reading the appropriate data from the look-up tables. This enables the stored relationships to be accessed without performing floating point calculations, which reduces the computational power needed to process the images, and enables the system to process the images more rapidly. Of course, if adequate computational power and/or time are available, the curve-fitted equations for the first and second relationships may be used directly to compute the high-energy value from the low-energy value, or vice versa.

In step S22, a set of pixels from the high-energy image and a corresponding set of pixels from the low-energy image is selected. The correspondence is such that the location of each pixel in the high-energy image is the same, respectively, as the location of each corresponding pixel in the low-energy image. The pixels that correspond to the references (which are located at pre-determined locations) are not selected.

The set of pixels (which may consist of one or more pixels) from the high-energy image are read and averaged. The corresponding set of pixels from the low-energy image are also read and averaged.

In step S24, a soft-tissue elimination process is used to create an image which contains only hard tissue. The soft-tissue elimination process takes the averaged pixels of the high-energy set and the averaged pixels of the low-energy set and, using the high-to-low energy look-up tables for hard tissue and soft tissue, calculates a hard tissue value for each of the pixels in the set. While the hard tissue value can be obtained from either the high-energy image ($IH_H$) or the low-energy image ($IL_H$), the low-energy image is preferred. A hard tissue image is then obtained in step S26 by storing the computed hard tissue values into the destination pixels that corresponded to the pixels of the selected set.

In step S28, a test is performed to determine whether any additional pixels remain in the image. If additional pixels remain, control returns to step S22. Otherwise, control passes to step S30.

Optionally, an additional image that contains only soft tissue may be created by eliminating the hard tissue from either the high-energy image or the low-energy image. This elimination may be accomplished by dividing each pixel of the high-energy (or low-energy) image by the hard tissue transmissivity value for that pixel.

Step S29 is performed after the hard tissue image is complete. In step S29, the pixels that correspond to bone are selected from the hard tissue image. This is accomplished by selecting only those pixels with transmissivities less than a predetermined threshold (which correspond to the low x-ray transmissivity of bone). Approximately 80% transmissivity is a suitable threshold, although other thresholds may be used. Of course, the pixels that correspond to the references (which are located at pre-determined locations) are not bone and are excluded.

Figure 6:
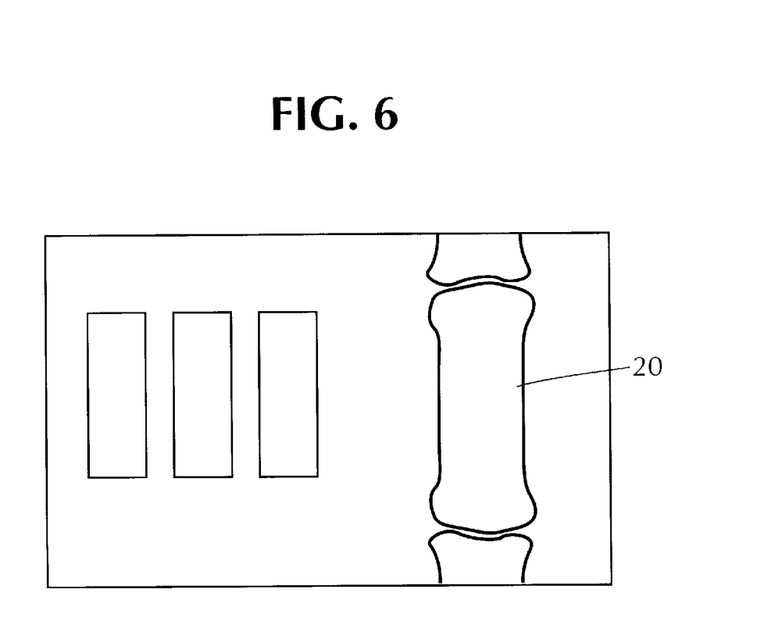
FIG. 6 depicts an x-ray image of a patient's finger.

Because the pixels that correspond to bone are automatically determined in this way, the bone will be recognized no matter where it appears in the image. As a result, the precise location of the bone within the image becomes less critical. By way of example, when the bone density of a patient's finger is measured (as depicted in FIG. 1), the image might contain the entire middle phalange as well as portions of the first and third phalanges (as depicted in FIG. 6). If, however, the finger is shifted, the image might contain only portions of the middle and first phalange. If the finger is shifted in the opposite direction, the image might contain only portions of the middle and third phalange. But no matter where the finger is positioned, the portion of the image that corresponds to bone will be recognized by the thresholding process. By automatically recognizing the portions of the image that correspond to bone, the present invention eliminates the need for an operator to designate which portion of the image should be used to compute the bone density. Eliminating this manual step demonstrates one of the drawbacks of traditional DEXA systems.

In step S30, a transmission-to-thickness function is created from the hard tissue reference data. While either the high-energy or the low-energy image may be used, the low-energy image is preferred. In addition, when the hard tissue reference includes a stepped wedge, the stepped wedge is preferred for creating this function. This function is created by reading pixels at different steps on the wedge from known locations in the image. The pixels in each step are averaged to obtain an average pixel intensity for each step. A curve fit is then performed using the average pixel intensity at each step as the 'x' value and the step height as the 'y' values. Fitting a quadratic curve to the data is preferred. Preferably, a look-up table is created based on the transmission-to-thickness function. The look-up table receives transmission (intensity) as an input and outputs thickness. An equivalent characteristic that is related to thickness (such as mass) may be used in place of thickness. When the hard tissue reference does not include a stepped wedge, data points from various heights along the hard linear wedge may be used instead.

Next, in step S32, the thickness of hard tissue above each pixel of bone in the hard tissue image is determined using the hard tissue image and the transmission-to-thickness look-up table (or function). The thickness for each pixel of bone is then averaged, the average is normalized to account for the area of a pixel, and the bone mineral density (BMD) is computed in Step S34 by multiplying the average thickness by the density of the hard tissue reference material (e.g., aluminum). The BMD is measured in units of mass per area, preferably in mg per square mm. The BMD may be converted to a t-score or a z-score that describes the degree of osteoporosis using well known techniques.

Figure 5:
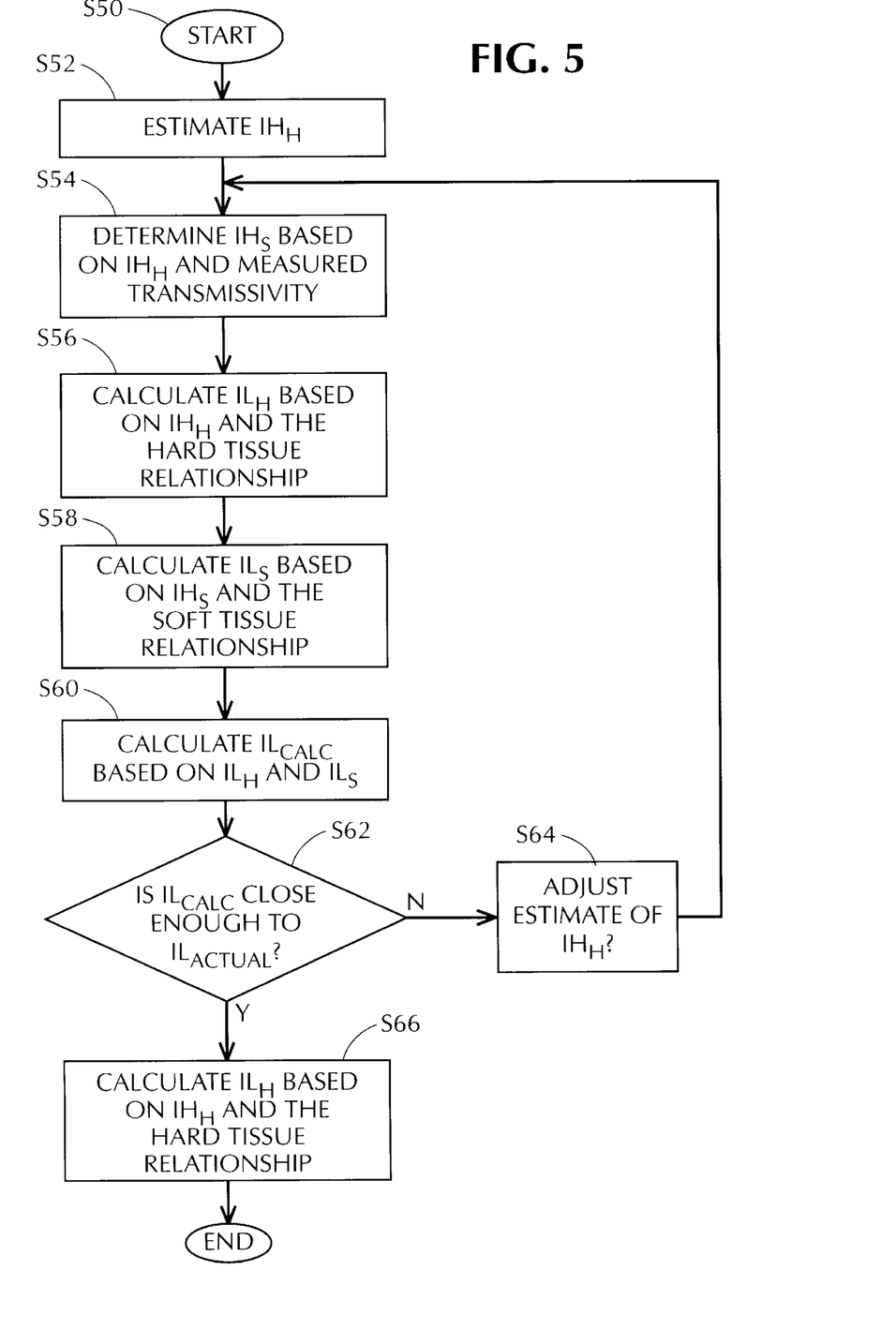
FIG. 5 is a flowchart of a preferred soft tissue elimination process in accordance with the present invention.

FIG. 5 depicts the preferred soft tissue elimination process. This process relies on the fact that bone and soft tissue react differently to high-energy and low-energy x-rays. The process uses a pair of references that approximate the x-ray absorption properties of bone and soft tissue. Two x-ray images of the subject and the pair of references are taken at different energies. The way particular thicknesses of bone and soft tissue reacts is established using the references. This information is used to eliminate soft tissue from an image.

To discover the relationship between the high-energy and low-energy responses for a particular material, the same pixel location is read from both the high and the low-energy images. Each reading represents the same combination of hard and soft tissue, but with different responses under different energies.

For each pixel in each image, the following relationship exists:

$$I = (I_H * I_S) * c$$

where I is the composite transmissivity for the pixel of interest; $I_H$ is the transmissivity of the hard tissue for the pixel of interest; $I_S$ is the transmissivity of the soft tissue pixel for the pixel of interest; and c is a constant that is preferably $1/2^{NBITS}$ (where NBITS is the number of bits in the word used to represent each pixel, e.g., 1/256 for 8 bits, 1/4096 for 12 bits, etc.).

Because there are two images (the high-energy image and the low-energy image), two actual measurements exist for each pixel. This results in two relationships:

$$IH = (IH_H * IH_S) * c \qquad \text{equation (1)}$$

and $$IL = (IL_H * IL_S) * c \qquad \text{equation (2)}$$

where IH is the measured high-energy image pixel; IL is the measured low-energy image pixel; $IH_H$ is the transmissivity of the hard tissue for the high-energy pixel; $IH_S$ is the transmissivity of the soft tissue for the high-energy pixel; $IL_H$ is the transmissivity of the hard tissue for the low-energy pixel; and $IL_S$ is the transmissivity of the soft tissue for the low-energy pixel.

$IH_H$ can be calculated for each pixel using the following process: First, in step S52, $IH_H$ is estimated. One acceptable starting point is setting $IH_H$ to IH/2*c. Another acceptable starting point is the square root of IH/c. As the process proceeds from pixel to pixel in the image, another excellent starting estimate is the value of $IH_H$ from a neighboring pixel, because the density of bone does not change rapidly over short distances.

Next, in step S54, $IH_S$ is computed to satisfy equation (1) based on the most recently estimated $IH_H$ and the measured IH. Of course, instead of estimating $IH_H$ and computing $IH_S$, it would be equivalent to estimate $IH_S$ and compute $IH_H$.

In step S56, $IH_H$ is converted into $IL_H$, using the high-energy to low-energy relationship for the hard tissue reference. In step S58, $IH_S$ is converted into $IL_S$, using the high-energy to low-energy relationship for the soft tissue reference. As described above, both of these relationships are preferably stored in look-up tables.

In step S60, $IL_{CALC}$ is calculated as follows:

$$IL_{CALC} = IL_H * IL_S * c$$

in step S62, $IL_{CALC}$ is compared to IL (called $IL_{ACTUAL}$ in FIG. 5). A preferred test to determine whether $IL_{CALC}$ is sufficiently close to IL is dividing $IL_{CALC}$ by IL, $$E = IL_{CALC} \div IL$$

and then checking whether the resulting quotient E is within the range of 1.0±0.001. If E is inside this range, then the most recent estimate of $IH_H$ is acceptable, and it is used as the hard tissue value for the high-energy image. If E is outside this range, then the most recent estimate of $IH_H$ is adjusted in step S64, and control returns to step S54 for another pass through the iterative process. A preferred adjustment is dividing the most recent estimate of $IH_H$ by the quotient E, and using the result as the new estimate of $IH_H$.

Once an acceptable estimate of $IH_H$ is obtained, $IL_H$ is computed based on $IH_H$ and the high-energy to low-energy relationship for the hard tissue reference in step S66. This is used as the resulting hard tissue value for the low-energy image. Of course, if the hard tissue value for the high-energy image is desired, then step S66 is omitted.

The results obtained using this soft tissue elimination process are superior to the results obtained using traditional soft tissue elimination processes. As described above in the background section, using a set of constants for the $\mu$ coefficients is a source of inaccuracy in traditional DEXA systems due to variations in the center frequency of the radiation and the wide bandwidth of the radiation. To obtain a more accurate model, the full range of frequencies contained in both the high-energy and low-energy images should be accounted for.

This process, in contrast to the traditional processes, does not rely on predetermined $\mu$ coefficients. Instead, the transmissivities of the soft tissue and the hard tissue are determined using the exact same radiation that is used to irradiate the bone. These characteristics are reflected in the look-up tables which are used in the soft tissue elimination process.

Numerous variations that are equivalent to the process described above can be readily envisioned. For example, instead of dividing $IL_{CALC}$ by IL in step 62 and dividing $IH_H$ by E in step S64, it would be equivalent to divide IL by $IL_{CALC}$ in step 62 and then multiply $IH_H$ by E in step S64. Other tests for closeness and other $IH_H$ estimate adjustments can also be readily envisioned. Another equivalent example could interchange the roles of equations (1) and (2) by estimating $IL_H$, and then continuing accordingly.

If the process fails to converge to a sufficiently close result within, for example, 20 iterations, the pixel may be discarded or set to black (i.e., the maximum value, which corresponds to air). If the non-convergence is an oscillation between two values, the average of those two values may be used as the result for that pixel.

A cache memory may be used to improve the performance of the soft tissue elimination process. For example, a cache can store $IH_H$ for a given IH and IL. The next time the process is started (at step S50), the cache can be checked for the answer. If the answer is present in the cache, it need not be computed. A cache may also be used to provide an improved initial estimate of $IH_H$ based on "near hits" with similar IH and IL values.

While the present invention has been described above in terms of specific embodiments, it is to be understood that the present invention is not limited to the disclosed embodiments. On the contrary, the present invention is intended to cover various modifications and equivalent structures included within the spirit and scope of the appended claims.

We claim:

1. A method of determining the density of a bone in a body part from a high-energy image and a low-energy image, the images including the body part, a hard tissue reference, and a soft tissue reference, the body part comprising bone and soft tissue, the method comprising the steps of:

determining high-energy and low-energy radiation transmissivity characteristics of varying thicknesses of the hard tissue reference and the soft tissue reference from the high-energy and low-energy images; and determining a density of the bone based on at least one pixel that corresponds to bone in the high-energy image, a corresponding at least one pixel in the low-energy image, and the determined transmissivity characteristics.

2. The method according to claim 1, wherein the at least one pixel that corresponds to bone is selected from pixels that have a transmissivity below a threshold and do not correspond to the references.

3. The method according to claim 2, wherein the threshold is approximately 80%.

4. The method according to claim 1, further comprising the step of determining relationships between the high-energy transmissivity characteristics and the low-energy radiation transmissivity characteristics for the hard tissue reference and for the soft tissue reference, wherein the step of determining a density of the bone is further based on the determined relationships.

5. The method according to claim 4, further comprising the step of storing the determined relationships in look up tables.

6. A method of measuring the density of a bone in a body part, the body part comprising bone and soft tissue, the method comprising the steps of:

obtaining a high-energy image of the body part and a hard tissue reference and a soft tissue reference by irradiating the body part and the references with high-energy radiation;

obtaining a low-energy image of the body part and the references by irradiating the body part and the references with low-energy radiation;

determining high-energy and low-energy radiation transmissivity characteristics of varying thicknesses of the hard tissue reference and the soft tissue reference from the high-energy and low-energy images; and determining a density of the bone based on at least one pixel that corresponds to bone in the high-energy image, a corresponding at least one pixel in the low-energy image, and the determined transmissivity characteristics.

7. The method according to claim 6, wherein the at least one pixel that corresponds to bone is selected from pixels that have a transmissivity below a threshold and do not correspond to the references.

8. The method according to claim 7, wherein the threshold is approximately 80%.

9. The method according to claim 6, further comprising the step of determining relationships between the high-energy transmissivity characteristics and the low-energy radiation transmissivity characteristics for the hard tissue reference and for the soft tissue reference, wherein the step of determining a density of the bone is further based on the determined relationships.

10. The method according to claim 9, further comprising the step of storing the determined relationships in look up tables.

11. The method according to claim 6, further comprising the steps of:

reading at least one pixel of interest in the high-energy image;

reading a corresponding at least one pixel in the low-energy image;

accessing a first function that relates the high-energy radiation transmissivity of the hard tissue reference to the low-energy radiation transmissivity of the hard tissue reference;

accessing a second function that relates the high-energy radiation transmissivity of the soft tissue reference to the low-energy radiation transmissivity of the soft tissue reference; and calculating a hard tissue value based on the at least one pixel of interest in the high-energy image, the corresponding at least one pixel in the low-energy image, the first function, and the second function.

12. The method according to claim 6, wherein the hard tissue reference comprises a stepped wedge and a linear wedge, and the soft tissue reference comprises a linear wedge.

13. The method according to claim 6, wherein the hard tissue reference comprises a stepped wedge, and the soft tissue reference comprises a linear wedge.

14. The method according to claim 6, wherein the soft tissue reference comprises soft tissue from the body part.

15. The method according to claim 6, wherein the hard tissue reference is aluminum, and the soft tissue reference is epoxy.

16. The method according to claim 6, wherein the step of obtaining the high energy image and the step of obtaining the low energy image are performed using an active pixel sensor.

17. The method according to claim 6, wherein the bone comprises at least a portion of a middle phalange of a middle finger of a patient's non-dominant hand.

18. A method of measuring the density of a bone in a body part, the body part comprising bone and soft tissue, the method comprising the steps of:

computing a first function that relates a high-energy radiation transmissivity of a hard tissue reference to a low-energy radiation transmissivity of the hard tissue reference, based on detected amounts of high-energy radiation and low-energy radiation transmitted through the hard tissue reference for at least some of a plurality of pixels located under the hard tissue reference;

computing a second function that relates a high-energy radiation transmissivity of a soft tissue reference to a low-energy radiation transmissivity of the soft tissue reference, based on detected amounts of high-energy radiation and low-energy radiation transmitted through the soft tissue reference for at least some of a plurality of pixels located under the soft tissue reference;

selecting a high-energy set of pixels from a high-energy image of the body part, and a corresponding low-energy set of pixels from a low-energy image of the body part;

computing a hard tissue value for the set of pixels based on the high-energy set, the low-energy set, the first function, and the second function;

computing a third function that relates an amount of radiation detected at a given pixel to the thickness of the hard tissue reference above the given pixel, based on an amount of radiation detected at each of a plurality of certain pixels and known thicknesses of the hard tissue reference above the certain pixels; and computing a bone density based on the third function and the hard tissue value for at least one pixel that corresponds to bone.

19. The method according to claim 18, wherein the hard tissue value for the at least one pixel that corresponds to bone is selected from pixels that have a transmissivity below a threshold and do not correspond to the references.

20. The method according to claim 19, wherein the threshold is approximately 80%.

21. The method according to claim 18, further comprising the steps of:

reading at least one pixel of interest in the high-energy image;

reading a corresponding at least one pixel in the low-energy image;

accessing the first function and the second function; and calculating a hard tissue value based on the at least one pixel of interest in the high-energy image, the corresponding at least one pixel in the low-energy image, the first function, and the second function.

22. The method according to claim 18, wherein the step of computing the bone density comprises the step of determining a thickness for the at least one pixel that corresponds to bone.

23. The method according to claim 18, further comprising the step of removing noise from the high-energy image and the low-energy image.

24. The method according to claim 18, further comprising the step of equalizing the high-energy image and the low-energy image.

25. The method according to claim 18, further comprising the step of storing the first function and the second function in look-up tables.

26. The method according to claim 18, further comprising the step of storing the third function in a look-up table.

27. The method according to claim 18, wherein the steps of computing the first function and computing the second function use a least-squares curve fit.

28. The method according to claim 18, wherein the selecting step and the step of computing a hard tissue value is performed for a plurality of sets of pixels from the high-energy image and the low-energy image.

29. The method according to claim 18, wherein the bone comprises at least a portion of a middle phalange of a middle finger of a patient's non-dominant hand.

30. A method of measuring the density of a bone in a body part, the body part comprising bone and soft tissue, the method comprising the steps of:

irradiating a hard tissue reference and a soft tissue reference with high-energy radiation;

detecting an amount of high-energy radiation transmitted through each tissue reference for each of a plurality of pixels located under each tissue reference;

irradiating the tissue references with low-energy radiation;

detecting an amount of low-energy radiation transmitted through each tissue reference for each of the plurality of pixels located under each tissue reference;

computing a first function that relates the high-energy radiation transmissivity of the hard tissue reference to the low-energy radiation transmissivity of the hard tissue reference, based on the detected amounts of high-energy radiation and low-energy radiation transmitted through the hard tissue reference for at least some of the plurality of pixels located under the hard tissue reference;

computing a second function that relates the high-energy radiation transmissivity of the soft tissue reference to the low-energy radiation transmissivity of the soft tissue reference, based on the detected amounts of high-energy radiation and low-energy radiation transmitted through the soft tissue reference for at least some of the plurality of pixels located under the soft tissue reference;

irradiating the body part with high-energy radiation;

obtaining a high-energy image by detecting an amount of high-energy radiation transmitted through the body part for each of a plurality of pixels located under the body part;

irradiating the body part with low-energy radiation;

obtaining a low-energy image by detecting an amount of low-energy radiation transmitted through the body part for each of the plurality of pixels located under the body part;

selecting a set of high-energy pixels from the high-energy image, and a corresponding set of low-energy pixels from the low-energy image;

computing a hard tissue value for the set of pixels based on the high-energy set, the low-energy set, the first function, and the second function;

computing a third function that relates an amount of radiation detected at a given pixel to the thickness of the hard tissue reference above the given pixel, based on an amount of radiation detected at each of a plurality of certain pixels and known thicknesses of the hard tissue reference above the certain pixels; and computing a bone density based on the third function and the hard tissue value for at least one pixel that corresponds to bone.

31. The method according to claim 30, wherein the hard tissue value for the at least one pixel that corresponds to bone is selected from pixels that have a transmissivity below a threshold and do not correspond to the references.

32. The method according to claim 31, wherein the threshold is approximately 80%.

33. The method according to claim 30, wherein the hard tissue reference comprises a stepped wedge and a linear wedge, the soft tissue reference comprises a linear wedge, the first function is computed using data corresponding to the hard linear wedge, the second function is computed using data corresponding to the soft linear wedge, and the third function is computed using data corresponding to the hard stepped wedge.

34. The method according to claim 30, wherein the hard tissue reference comprises a stepped wedge, and the soft tissue reference comprises a linear wedge.

35. The method according to claim 30, wherein the soft tissue reference comprises soft tissue from the body part.

36. The method according to claim 30, wherein the hard tissue reference is aluminum, and the soft tissue reference is epoxy.

37. The method according to claim 30, wherein the step of obtaining the high energy image and the step of obtaining the low energy image are performed using an active pixel sensor.

38. An apparatus for determining the density of a bone in a body part from a high-energy image and a low-energy image, the images including the body part, a hard tissue reference, and a soft tissue reference, the body part comprising bone and soft tissue, the apparatus comprising:

means for determining high-energy and low-energy radiation transmissivity characteristics of varying thicknesses of the hard tissue reference and the soft tissue reference from the high-energy and low-energy images; and means for determining a density of the bone based on at least one pixel that corresponds to bone in the high-energy image, a corresponding at least one pixel in the low-energy image, and the determined transmissivity characteristics.

39. The apparatus according to claim 38, wherein the at least one pixel that corresponds to bone is selected from pixels that have a transmissivity below a threshold and do not correspond to the references.

40. The apparatus according to claim 39, wherein the threshold is approximately 80%.

41. The apparatus according to claim 38, further comprising means for determining relationships between the high-energy transmissivity characteristics and the low-energy radiation transmissivity characteristics for the hard tissue reference and for the soft tissue reference, wherein the means for determining a density of the bone is further based on the determined relationships.

42. The apparatus according to claim 41, further comprising memory means for storing the determined relationships in look up tables.

43. An apparatus for measuring the density of a bone in a body part, the body part comprising bone and soft tissue, comprising:

means for obtaining a high-energy image of the body part and a hard tissue reference and a soft tissue reference by irradiating the body part and the references with high-energy radiation;

means for obtaining a low-energy image of the body part and the references by irradiating the body part and the references with low-energy radiation;

means for determining high-energy and low-energy radiation transmissivity characteristics of varying thicknesses of the hard tissue reference and the soft tissue reference from the high-energy and low-energy images; and means for determining a density of the bone based on at least one pixel that corresponds to bone in the high-energy image, a corresponding at least one pixel in the low-energy image, and the determined transmissivity characteristics.

44. The apparatus according to claim 43, wherein the at least one pixel that corresponds to bone is selected from pixels that have a transmissivity below a threshold and do not correspond to the references.

45. The apparatus according to claim 44, wherein the threshold is approximately 80%.

46. The apparatus according to claim 43, further comprising means for determining relationships between the high-energy transmissivity characteristics and the low-energy radiation transmissivity characteristics for the hard tissue reference and for the soft tissue reference, wherein the means for determining a density of the bone is further based on the determined relationships.

47. The apparatus according to claim 46, further comprising memory means for storing the determined relationships in look up tables.

48. The apparatus according to claim 43, wherein the means for obtaining the high energy image and the means for obtaining the low energy image comprise an active pixel sensor.

49. A method of determining the radiation transmissivity of a bone in a body part, comprising the steps of:

reading at least one pixel of interest in a high-energy image of the body part;

reading a corresponding at least one pixel in a low-energy image of the body part;

accessing a first function that relates a high-energy radiation transmissivity of a hard tissue reference to a low-energy radiation transmissivity of the hard tissue reference;

accessing a second function that relates a high-energy radiation transmissivity of a soft tissue reference to a low-energy radiation transmissivity of the soft tissue reference; and calculating a hard tissue value based on the at least one pixel of interest in the high-energy image, the corresponding at least one pixel in the low-energy image, the first function, and the second function.

50. The method according to claim 49, wherein the step of accessing the first function comprises the step of reading from a first look-up table, and the step of accessing the second function comprises the step of reading from a second look-up table.

51. An apparatus for determining the radiation transmissivity of a bone in a body part, comprising:

means for reading at least one pixel of interest in a high-energy image of the body part;

means for reading a corresponding at least one pixel in a low-energy image of the body part;

memory means for storing a first function that relates a high-energy radiation transmissivity of a hard tissue reference to a low-energy radiation transmissivity of the hard tissue reference and a second function that relates a high-energy radiation transmissivity of a soft tissue reference to a low-energy radiation transmissivity of the soft tissue reference; and calculating means for calculating a hard tissue value based on the at least one pixel of interest in the high-energy image, the corresponding at least one pixel in the low-energy image of the body part, the first function, and the second function.

52. The apparatus according to claim 51, wherein the memory means comprises a look-up table.

53. A method of determining the radiation transmissivity of a bone in a body part using a pixel of interest in a first-energy image of the body part, a corresponding pixel in a second-energy image of the body part, a first function that relates the first-energy radiation transmissivity of a first tissue reference to the second-energy radiation transmissivity of the first tissue reference, and a second function that relates the first-energy radiation transmissivity of a second tissue reference to the second-energy radiation transmissivity of the second tissue reference, the method comprising the steps of:

(a) estimating a first-energy radiation transmissivity of the first tissue for a pixel of interest;

(b) determining a first-energy radiation transmissivity of the second tissue for the pixel of interest based on the estimated first-energy radiation transmissivity of the first tissue and a measured first-energy transmissivity of the pixel of interest;

(c) calculating, for the pixel of interest, a second-energy radiation transmissivity of the first tissue and a second-energy radiation transmissivity of the second tissue based on the estimated first-energy radiation transmissivity of the first tissue, the determined first-energy radiation transmissivity of the second tissue, the first function, and the second function;

(d) calculating a composite second-energy transmissivity for the pixel of interest based on the calculated second-energy radiation transmissivity of the first tissue and the second-energy radiation transmissivity of the second tissue;

(e) comparing the calculated composite second-energy transmissivity to a measured second-energy transmissivity of the pixel of interest, and determining whether the calculated composite is sufficiently close to the measured value; and (f) adjusting the estimate of the first-energy radiation transmissivity of the first tissue and repeating steps (b) through (f) when it is determined, in said comparing step, that the calculated composite is not sufficiently close to the measured value.

54. The method according to claim 53, repeated for a plurality of pixels of interest in the first-energy image and a corresponding plurality of pixels in the second-energy image.

55. The method according to claim 54, further comprising the step of calculating a second-energy radiation transmissivity of the first tissue for the pixel of interest based on a final value of the first-energy radiation transmissivity of the first tissue and the first function.

* * * * *

UNITED STATES PATENT AND TRADEMARK OFFICE
CERTIFICATE OF CORRECTION

PATENT NO. : 5,852,647

DATED : December 22, 1998

INVENTOR(S) : DAVID B. SCHICK ET AL.

It is certified that error appears in the above-identified patent and that said Letters Patent is hereby corrected as shown below:

COLUMN 1

Line 21, "an Ordinary x-rays" should read --Ordinary x-ray--.
    Line 41, "mH" should read --$m_H$--.

COLUMN 4

Line 62, "referably" should read --preferably--.
    Line 66, "ources" should read --sources--.

COLUMN 5

Line 6, "Zinc" should read --zinc--.

COLUMN 9

Line 33, "step 62" should read --step S62--.
    Line 34, "step 62" should read --step S62--.

COLUMN 11

Line 24, "high energy" should read --high-energy--.
    Line 25, "low energy" should read --low-energy--.

UNITED STATES PATENT AND TRADEMARK OFFICE
CERTIFICATE OF CORRECTION

PATENT NO. : 5,852,647

DATED : December 22, 1998

INVENTOR(S) : DAVID B. SCHICK ET AL.

It is certified that error appears in the above-identified patent and that said Letters Patent is hereby corrected as shown below:

COLUMN 13

Line 52, "high energy" should read --high-energy--.
    Line 53, "low energy" should read --low-energy--.

COLUMN 14

Line 54, "high energy" should read --high-energy--.
    Line 55, "low energy" should read --low-energy--.

Signed and Sealed this

Fourteenth Day of September, 1999

Attest:

Q. TODD DICKINSON

*Attesting Officer*     *Acting Commissioner of Patents and Trademarks*